US010359386B2

(12) United States Patent
Marashdeh et al.

(10) Patent No.: US 10,359,386 B2
(45) Date of Patent: *Jul. 23, 2019

(54) MODULAR STRETCHABLE AND FLEXIBLE CAPACITANCE SENSORS FOR USE WITH ELECTRICAL CAPACITANCE VOLUME TOMOGRAPHY AND CAPACITANCE SENSING APPLICATIONS

(71) Applicant: Tech4Imaging LLC, Columbus, OH (US)

(72) Inventors: Qussai Marashdeh, Columbus, OH (US); Yousef Alghothani, Columbus, OH (US)

(73) Assignee: Tech4Imaging LLC, Columbus, OH (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/591,224

(22) Filed: May 10, 2017

(65) Prior Publication Data
US 2017/0241935 A1   Aug. 24, 2017

Related U.S. Application Data

(63) Continuation of application No. 14/746,329, filed on Jun. 22, 2015, now Pat. No. 9,664,635, which is a
(Continued)

(51) Int. Cl.
*G01R 27/26* (2006.01)
*G01N 27/22* (2006.01)
(Continued)

(52) U.S. Cl.
CPC ......... *G01N 27/226* (2013.01); *A61B 5/0536* (2013.01); *G01N 27/22* (2013.01);
(Continued)

(58) Field of Classification Search
USPC ......................................... 324/662, 663, 686
See application file for complete search history.

(56) References Cited

U.S. PATENT DOCUMENTS

| 5,130,661 A | 7/1992 | Beck et al. |
| 5,262,730 A | 11/1993 | Smith et al. |

(Continued)

FOREIGN PATENT DOCUMENTS

| CN | 102954854 A | 3/2013 |
| EP | 0606115 A1 | 7/1994 |

(Continued)

OTHER PUBLICATIONS

Marashdeh, et al., "On the ECT Sensor Based Dual Imaging Modality System for Electrical Permittivity and Conductivity Measurements", 2006, pp. 1-6, The Ohio State University, Columbus, Ohio.

(Continued)

*Primary Examiner* — Vincent Q Nguyen
(74) *Attorney, Agent, or Firm* — Standley Law Group LLP

(57) ABSTRACT

A flexible capacitance sensor having multiple layers for communicating signals to a data acquisition system for reconstructing an image of an area or object located in a subject being sensed, the flexible capacitance sensor having a flexible layer of capacitance plates; a flexible shielding ground layer next to the layer of capacitance plates; a flexible layer of signal traces next to the shielding ground layer, where the layer of signal traces has a plurality of trace lines; and where the capacitance sensor is flexible and adapted to be wrapped around the subject being sensed. The sensor is adapted to communicate signals via the plurality of trace lines to a data acquisition system for providing an image of the area or object between the capacitance plates.

14 Claims, 10 Drawing Sheets

Related U.S. Application Data continuation of application No. 13/965,636, filed on Aug. 13, 2013, now Pat. No. 9,110,115.

(51) Int. Cl.
  *A61B 5/053* (2006.01)
  *G06T 11/00* (2006.01)
  *G01D 5/24* (2006.01)
  *A61B 5/00* (2006.01)
  *G06T 15/08* (2011.01)

(52) U.S. Cl.
  CPC ........ *G01R 27/2605* (2013.01); *G06T 11/003* (2013.01); *A61B 5/6802* (2013.01); *G01D 5/24* (2013.01); *G06T 15/08* (2013.01); *G06T 2211/412* (2013.01); *G06T 2211/428* (2013.01)

(56) References Cited

U.S. PATENT DOCUMENTS

| | | | |
|---|---|---|---|
| 5,279,163 | A | 1/1994 | D'Antonio et al. |
| 6,208,204 | B1 | 3/2001 | Suzuki et al. |
| 7,424,462 | B2 | 9/2008 | Avni et al. |
| 7,684,846 | B2 | 3/2010 | Johnson et al. |
| 8,461,852 | B2 | 6/2013 | Yang et al. |
| 8,508,238 | B2 | 8/2013 | Mahalingam et al. |
| 8,519,722 | B1 | 8/2013 | Prendergast |
| 8,614,707 | B2 | 12/2013 | Warsito |
| 8,867,928 | B2 | 10/2014 | Piehler |
| 9,016,143 | B2 | 4/2015 | Mamigonians |
| 9,170,224 | B2 | 10/2015 | Fan et al. |
| 9,579,038 | B2 | 2/2017 | Brunner et al. |
| 9,581,560 | B2 | 2/2017 | Fan et al. |
| 2002/0028010 | A1 | 3/2002 | Toida |
| 2003/0020493 | A1 | 1/2003 | Haase et al. |
| 2003/0173958 | A1 | 9/2003 | Goldfine et al. |
| 2004/0233191 | A1 | 11/2004 | Mukherjee |
| 2005/0167588 | A1 | 8/2005 | Donnangelo |
| 2007/0024278 | A1 | 2/2007 | Walters et al. |
| 2007/0133746 | A1 | 6/2007 | Ortiz Aleman et al. |
| 2008/0116995 | A1 | 5/2008 | Kim et al. |
| 2009/0272028 | A1 | 11/2009 | Drozd et al. |
| 2010/0097374 | A1 | 4/2010 | Warsito |
| 2010/0132473 | A1 | 6/2010 | Willcox |
| 2010/0148804 | A1 | 6/2010 | Jakoby et al. |
| 2010/0332170 | A1 | 12/2010 | Gao et al. |
| 2011/0109911 | A1 | 5/2011 | Podoleanu |
| 2012/0268135 | A1 | 10/2012 | Marsala et al. |
| 2013/0085365 | A1 | 4/2013 | Marashdeh |
| 2013/0187641 | A1 | 7/2013 | Singer |
| 2013/0275082 | A1 | 10/2013 | Follmer |
| 2014/0361793 | A1 | 12/2014 | Marashdeh et al. |
| 2014/0365152 | A1 | 12/2014 | Marashdeh et al. |
| 2015/0338364 | A1 | 11/2015 | Fan et al. |
| 2016/0025663 | A1 | 1/2016 | Lehikoinen et al. |
| 2016/0091448 | A1 | 3/2016 | Soleimani |
| 2016/0206227 | A1 | 7/2016 | Marashdeh et al. |

FOREIGN PATENT DOCUMENTS

| | | |
|---|---|---|
| WO | 2010007096 A3 | 1/2010 |
| WO | 2011002793 A1 | 1/2011 |

OTHER PUBLICATIONS

Warsito, et al., "Electrical Capacitance Volume Tomography", 2007, pp. 1-9.
Huang et al., Design of Sensor Electronics for Electrical Capacitance Tomography, IEE Proceedings G (Circuits, Devices and Systems), vol. 139, Issue 1, Feb. 1992, p. 83-88.
Marashdeh, Q. et al., Adaptive Electrical Capacitance Volume Tomography, IEEE Sensors Journal, Apr. 2014, pp. 1253-1259, vol. 14, No. 4.
Yang, W. et al., Image Reconstruction Algorithms for Electrical Capacitance Tomography, Measurement Science and Technology 14, 2003, pp. R1-R13.
Xie, C. et al., Electrical Capacitance Tomography for Flow Imaging: System Model for Development of Image Reconstruction Algorithms and Design of Primary Sensors, IEEE Proceedings-G, Feb. 1992, pp. 89-98, vol. 139, No. 1.
Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.
Covilakam, M., "Evaluation of Structural Monitoring Methods for Large Diameter Water Transmission Pipelines", Dec. 2011, The University of Texas at Arlington.
Gunes, C. et al., A Comparison Between Electrical Capacitance Tomography and Displacement-Current Phase Tomography, IEEE Sensors Journal, Dec. 15, 2017, vol. 17, No. 24.
Wang, F. et al., Electrical Capacitance Volume Tomography: Design and Applications, Sensors, 2010 pp. 1890-1917.
Wikipedia, Electrical Capacitance Volume Tomography, https://en.wikipedia.org/w/index.php?title=Electrical_capacitance_volume_tomography&oldid=868112998, site visited Dec. 7, 2018.

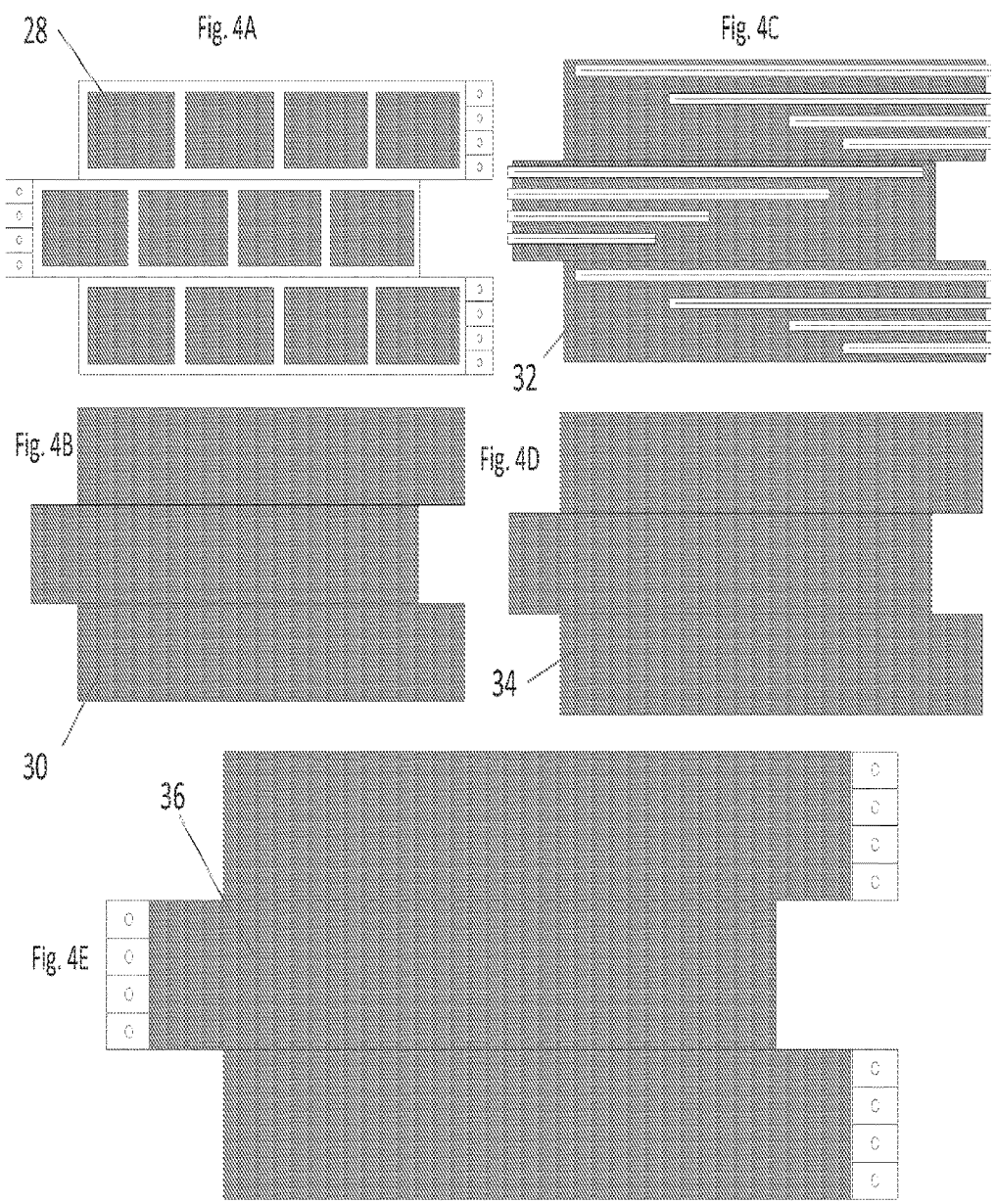

MODULAR STRETCHABLE AND FLEXIBLE CAPACITANCE SENSORS FOR USE WITH ELECTRICAL CAPACITANCE VOLUME TOMOGRAPHY AND CAPACITANCE SENSING APPLICATIONS

CROSS-REFERENCE TO RELATED APPLICATIONS

This application is a continuation of U.S. application Ser. No. 14/746,329, filed on Jun. 22, 2015, which is a continuation of U.S. application Ser. No. 13/965,636, filed on Aug. 13, 2013. Each of which are herein incorporated by reference as if recited in their entirety.

BACKGROUND OF THE INVENTIVE FIELD

Electrical Capacitance Tomography (ECT) is the reconstruction of material concentrations of dielectric physical properties in the imaging domain by inversion of capacitance data from a capacitance sensor.

Volume capacitance imaging or ECVT is the direct 3D reconstruction of volume concentration or physical properties in the imaging domain utilizing 3D features in the ECVT sensor design.

Adaptive ECVT is an advanced technology that introduces a new dimension into 3D sensor design by applying voltages of different frequencies, amplitudes, and/or phases to capacitance plate segments. Adaptive sensors can provide a virtually infinite number of independent capacitance measurements of the flow field or imaging volume through which high resolution images can be obtained.

ECVT sensors were developed to distribute electric field in three dimensions for reconstruction of dielectric constant distribution in an imaging domain.

ECVT sensors can utilize different plate shapes and distributions in multiple layers to target a volume for imaging.

SUMMARY OF THE EXEMPLARY EMBODIMENTS

The present invention is directed to process tomography and, in particular, to Electrical Capacitance Volume Tomography (ECVT) and adaptive ECVT sensors and using design techniques for realizing flexible, wearable, stretchable, and modular ECVT sensors.

Dynamic ECVT is a technology that senses measured capacitances between sensor plates to generate a whole volume image of the region. ECVT technology has been applied in providing images of objects moving through a pipe for example. ECVT has provided insight into multiphase flow phenomena in many industrial processes, including pneumatic conveying, oil pipe lines, fluidized beds, bubble columns and many other chemical and biochemical processes (the multiphase flow often being in a combination of gas, liquid, and solid states). ECVT may also be used for imaging biological processes and tissues.

Capacitance sensing sensors were designed previously to address fixed structure applications surrounding a dynamic flow component. The design of the present invention includes the integration of all plates, connectors, resistors, and shielding layers into one flexible or stretchable element. The present invention provides an innovative design with features through which the sensor can be used repeatedly and on different subjects (columns, pipes, organs, or limbs, etc.) through relatively simple installations. Specifically, features of the preferred embodiment of the present invention includes the integration of all components of a capacitance sensor into one element (of multiple layers) for handling by users, a modular feature where different plates configurations can be easily assembled, a wearable feature where sensors can be placed by users at different parts of the human body, and stretchable feature where sensors can be expanded in different directions. Details of these features are described below.

The integrative design of the present invention combines all elements of a capacitance sensor into one flexible sheet that can be used repeatedly. This flexible sheet in the preferred embodiment contains multiple layers including the layers of capacitance plates, isolated signal traces, ground shielding, isolative/resistive layers between conductive layers, a ground layer and low profile connectors for connecting signal traces to low profile coaxial cables. The plate layer contains design of capacitance sensors aimed at distributing the electric field in three dimensions. Traces can be separated from each other by ground to reduce capacitive coupling. The isolative/resistive layer preferably provides separation between plate layer, signal trace layer, and shield/ground layer. The resistance provides a path for discharge of static charges. The shielding ground layer preferably provides isolation for the capacitance sensors from outside capacitance coupling or electric noise. In one embodiment, the low profile connectors connect the sensor plates to data acquisition system through signal traces separated by ground. The ground between traces is aimed at reducing coupling between capacitance plates. The integrative design here enables capacitance sensors to be used easily for wrapping around different geometries. It also provides a means for a wearable feature where sensors can be placed on the human body in a low profile manner. It also provides a stretchable sensor where sensor elements can be extended for applications where object intended for imaging may change in size or geometry. This integrative approach can be applied for ECVT sensors of different designs and varying number of plates.

The integrative design of the present invention also preferably includes a modular feature where plates fabricated in an integrative approach can be layered separately for forming an equivalent plate. Such feature enables changing sensor design using modular sensors/plates.

The present invention also preferably includes a stretchable feature where sensor plates and layers are fabricated from stretchable materials. For example, stretchable materials can be a formed of stretchable flexible boards or flexible metal meshes used for fabricating conductive layers. The flexibility can also be provided by connecting flexible integrative sensor sections using stretchable connections. Flexibility can also be provided using conductive spray on stretchable isolative materials (like rubber or elastic material or even stretchable fabric) to form layers of integrative sensors as explained above.

The interactive design of the present invention also preferably includes a combination of traditional solid layered printed circuit boards and flexible or stretchable sensors. Applications of such combination include addressing an object for imaging where a part of it is fixed and another is expanding.

The integrative design of the present invention also enables measuring of capacitance signals from an Adaptive Electrical Capacitance Volume Tomography (AECVT) sensor.

BRIEF DESCRIPTION OF THE DRAWINGS

A better understanding of an exemplary embodiment will be obtained from a reading of the following detailed descrip

FIGS. 4A-E illustrate one embodiment of a 24 channel sensor with layers separated out individually for illustration.

DETAILED DESCRIPTION OF THE PREFERRED EMBODIMENTS

Figure 1:
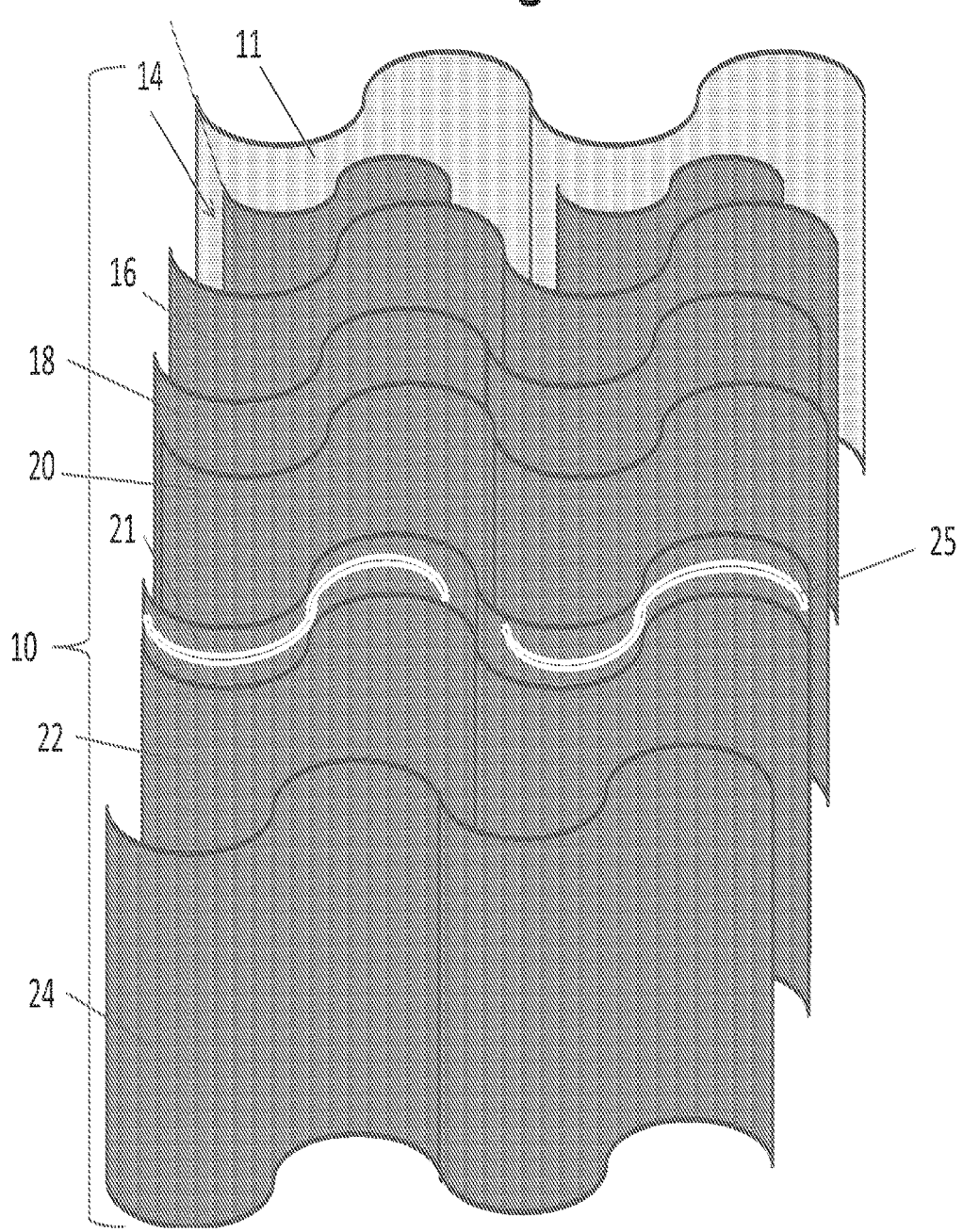
- FIG. 1 illustrates one embodiment of a flexible integrative sensor design of the present invention.

FIG. 1 illustrates one embodiment of an integrative sensor design 10 of the present invention having with two capacitance plates 12. More plates can be incorporated using the concepts discussed herein to form virtually any number of sensor configurations of differing shapes and sizes. In the preferred embodiment, the capacitance sensor includes multiple layers for forming a capacitance sensor. For example, the layers may include a flexible insulation layer 11, plate layer 14, isolative/resistor layer 16, a shielding ground layer 18, a second isolative layer 20, a flex signal trace layer 21, an insulation layer 22 and a ground layer 24 and connectors integrated into one flexible board 10. The plates are preferably made up of conductive material such as copper (metals), conductive liquid, conductive ink, or conductive spray. In the preferred embodiment, signal traces are used in a separate layer with ground shielding in between them for isolation of capacitance coupling. A trace is a conductive line that is imbedded in one of the sensors layers and acts as a means to conduct electric signals from plates to data acquisition system or from plates to low profile connectors. Low profile connectors are preferably used for interfacing strip-lines with coaxial cables for connecting with a data acquisition system for collection sensor readings.

In the embodiment shown in 1, the first insulation layer 11 separates the capacitance plates from the object or flow being imaged. The second layer is the capacitance plates layer 14. Capacitance plates 12 are preferably composed of conductive material and are typically made from metals. In one embodiment, the plates can be made from conductive spray on a nonconductive layer. The third layer is an isolative layer 16 or resistive layer. This layer separates the plates from the ground layer. The isolative layer can be made resistive so it provides a path to discharge static charges from the plates to the ground. The fourth ground layer 18 separates the traces from the plates so they don't couple. The fifth layer is again an isolative layer 20 that separates the ground layer from the traces layer. The sixth layer is the traces layer 21. In this layer trace lines 25 are introduced to communicate electric signals from the plates to data acquisition system or from plates to low profile connectors. Gaps between traces in this layer are preferably filled with ground lines to reduce coupling between trace lines. The seventh layer is again isolative 22. The eighth layer is a ground layer 24 to shield the sensor from outside interference and from trace lines cross-coupling. In the preferred embodiment, all layers are connected together by a thin layer of adhesive typically used in flexible circuit boards technology. The adhesive layer can also serve as an isolative layer. Another embodiment involves plates, ground, and traces sprayed or printed on separate layers using conductive spray or ink and then layering those layers with insulation between them. Such separate layers can be elastic of stretchable materials.

Figure 2:
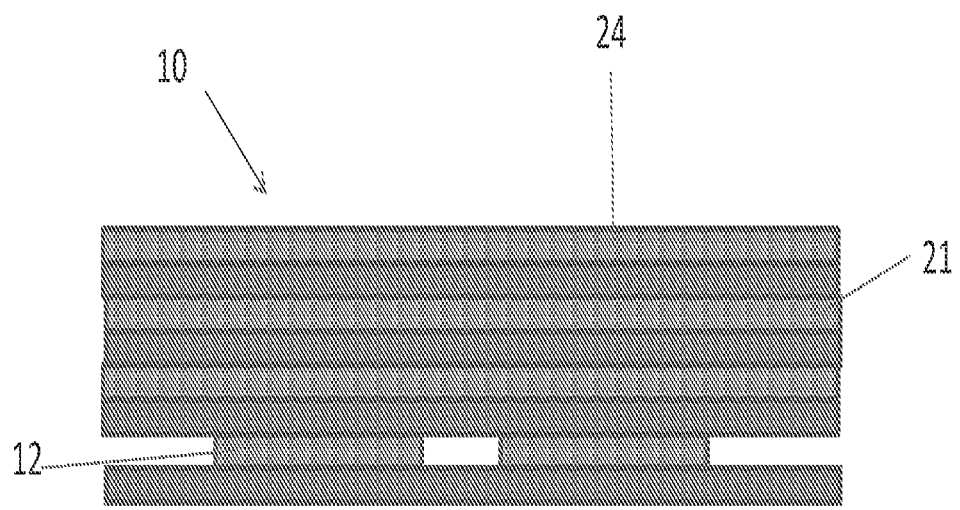
FIG. 2 illustrates one embodiment for a sensor with a 2D profile that shows the different layers in the integrative sensor design depicted in FIG. 1.

FIG. 2 illustrates one embodiment for a sensor with a 2D profile that shows the different layers in integrative sensor design depicted in FIG. 1.

Figure 3:
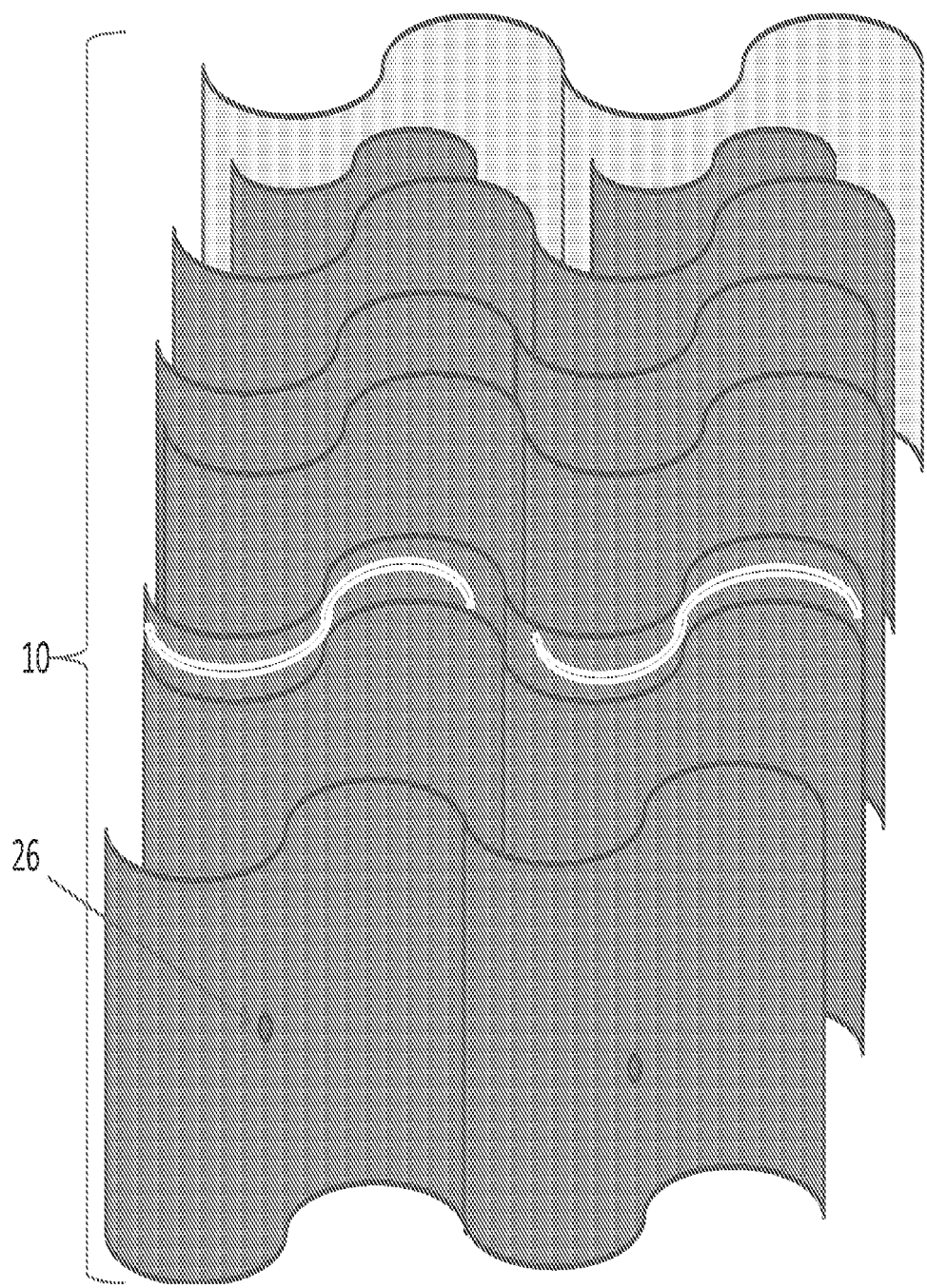
FIG. 3 illustrates one embodiment of the sensor with through holes for interfacing coaxial cables with plates.

FIG. 3 illustrates one embodiment of the sensor with through holes 26 for interfacing coaxial cables with plates.

FIGS. 4A-E illustrate one embodiment of a 24 channel sensor with layers separated out individually for illustration. Layers are preferably separated by isolative material and they include FIG. 4A plates layer 28, FIG. 4B ground layer 30, FIG. 4C signal trace layer 32, and FIG. 4D ground shielding layer 34. The integrated sensor with the layers combined is shown in the FIG. 4E at 36.

Figure 5A:
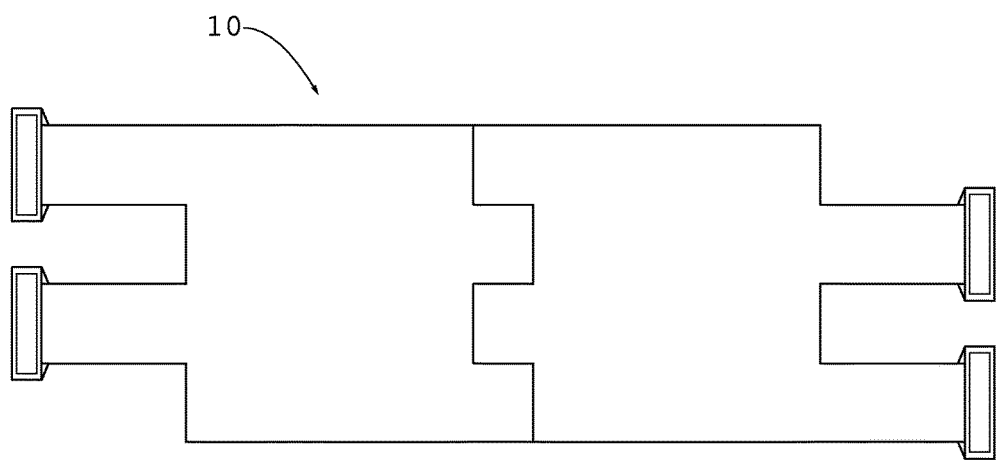
FIGS. 5A-B illustrate one embodiment of an integrated flexible capacitance sensor for ECVT applications.
Figure 5B:
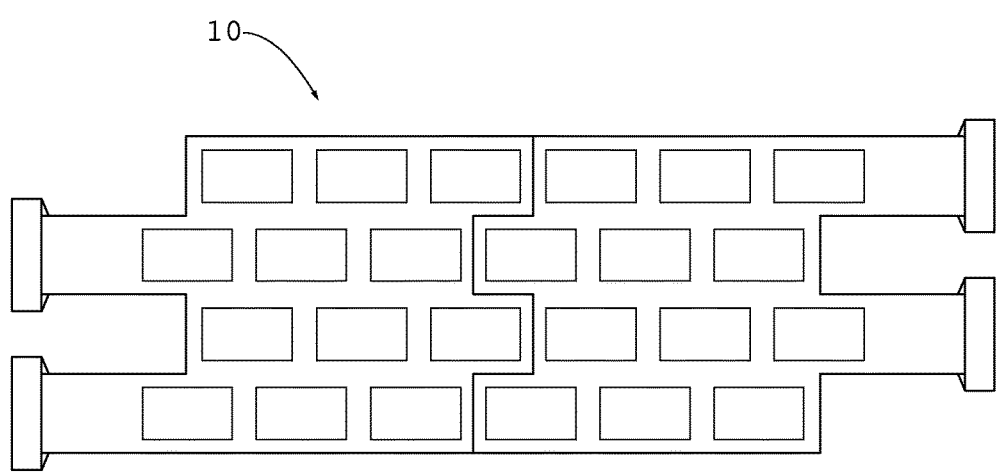

FIGS. 5A-B illustrate one embodiment of an integrated flexible capacitance sensor for ECVT applications. FIGS. 5A and 5B illustrate the front and back sides of the fabricated design of FIG. 4E, respectively, with the layers and components of an ECVT sensor integrated in one flexible circuit.

Figure 6A:
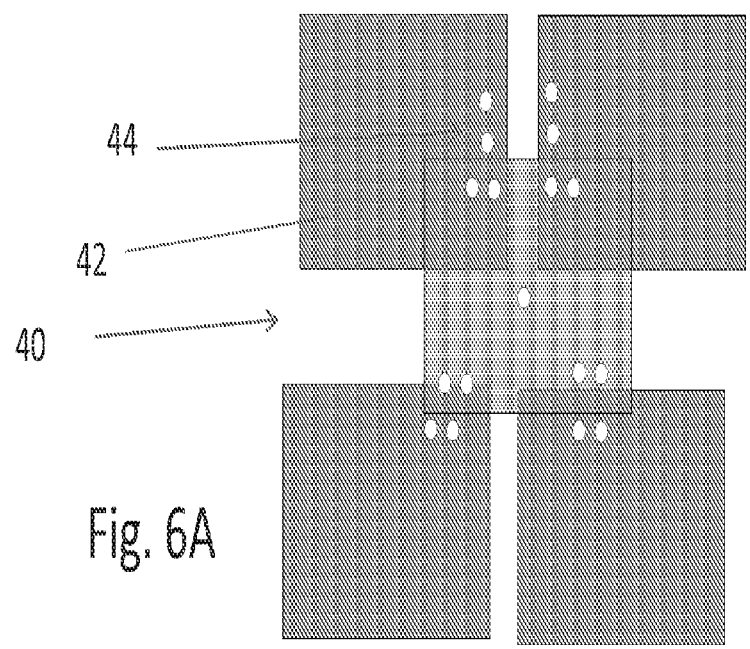
FIGS. 6A-B illustrate one embodiment of a sensor of the present invention configured into one capacitance plate by combining multiple flexible integrative sensors into one equivalent plate.
Figure 6B:
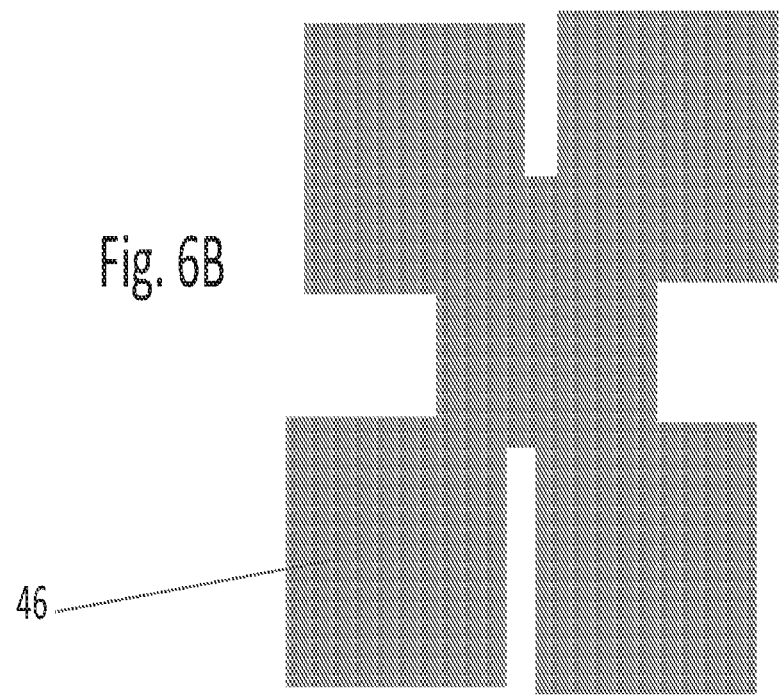

FIGS. 6A-B illustrate one embodiment of a sensor of the present invention configured into one capacitance plate by combining multiple flexible integrative sensors 42 into one equivalent plate. This modular approach can be used for sensors with multiple plates to form a modular ECVT sensor. Modular sections 42 are combined together by connecting plates, traces, and ground of each modular section to another modular section. Through holes 44 provide means to connecting inner layers of a modular section. For example, a through hole for the trace of a modular section provides a path directly to the trace and bypassing in-between layers. Modular sections also can be connecting through low profile PCB connectors where each layer in one modular section is connected to the same (equivalent) layer of another modular section. Modular sections can also be connected through stretchable lines for introducing elasticity to the design. An equivalent resulting sensor plate from combining modular sections is shown at 46.

Figure 7A:
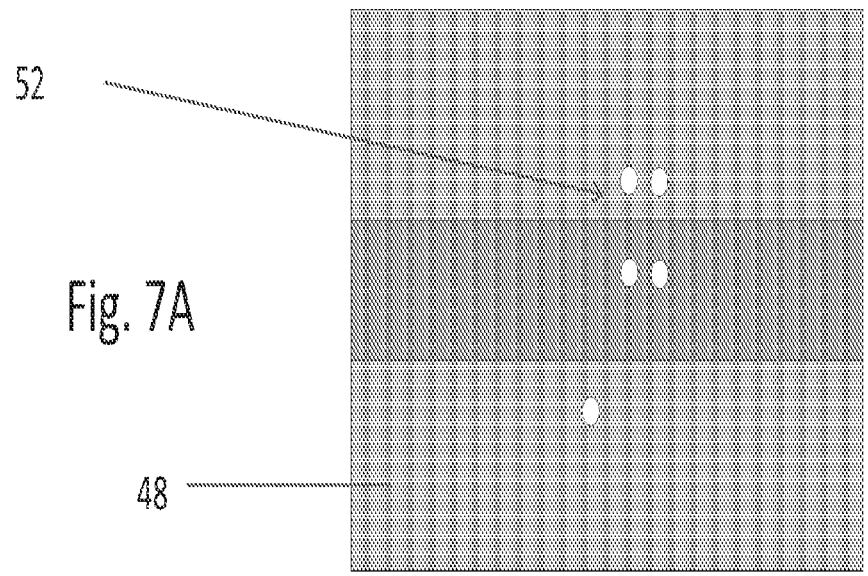
FIGS. 7A-B illustrate one sensor embodiment for an expandable sensor design with modular plates.
Figure 7B:
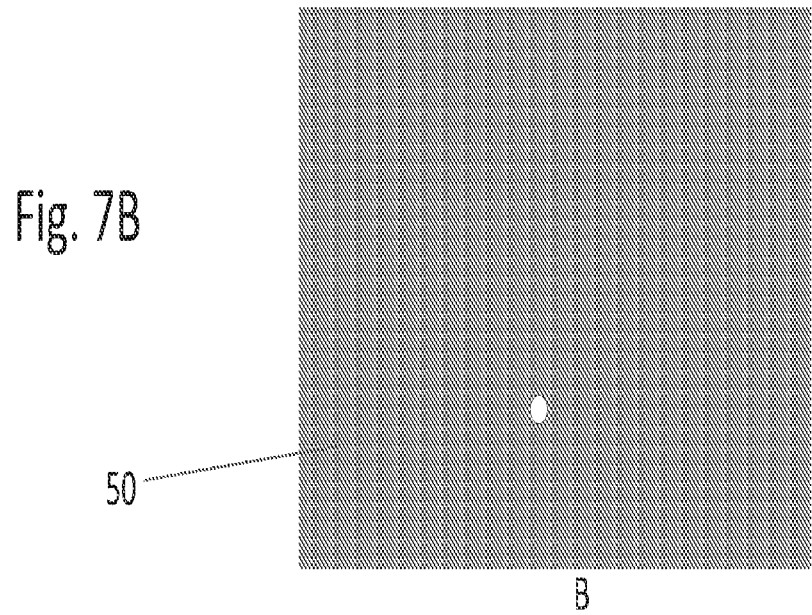

FIGS. 7A-B illustrate one sensor embodiment for an expandable sensor design where modular plates 48 are connected to form an equivalent plate 50 where the equivalent plate can change in size by moving modular plates with respect to each other. Through holes 52 provide paths to different layers in each modular section. Layers from each modular section are preferably connected together using corresponding through holes. Lines used to connect different modular sections can be flexible or stretchable to provide room for movement of modular plates. Modular plates can be of any shape or size.

Figure 8:
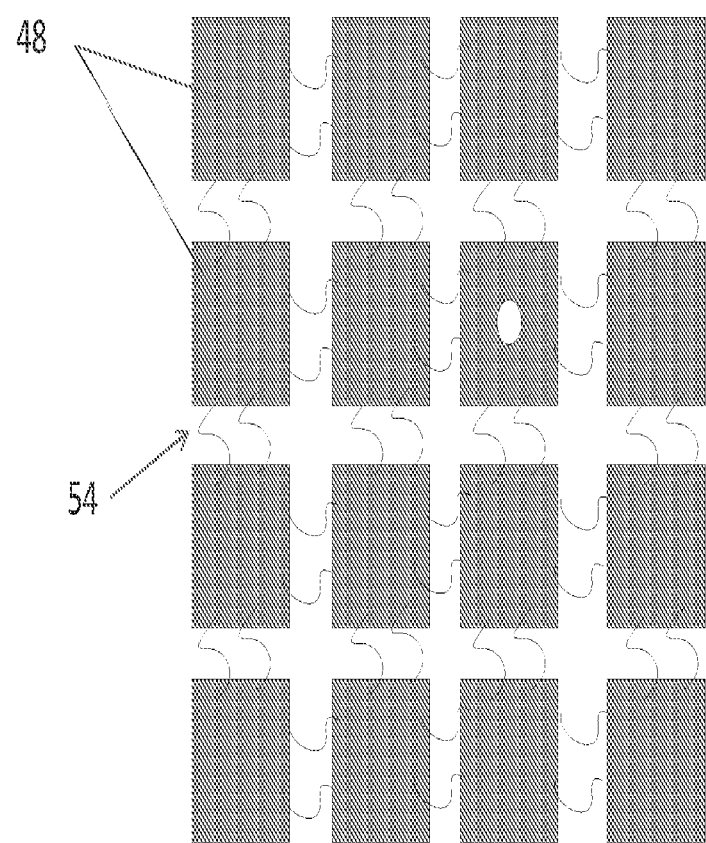
FIG. 8 illustrates one embodiment of a capacitance sensor of the present invention having integrative elements connected using stretchable connectors.

FIG. 8 illustrates one embodiment of a capacitance sensor of the present invention having integrative elements connected using stretchable connectors 54 for forming a stretchable ECVT sensor. Here, modular elements similar to ones described in FIGS. 7A and 7B are connected using stretchable lines to connect through holes of different modular section together. The stretchability of connecting lines renders the new formed plate as stretchable. Stretchable lines can be made of elastic material soaked in conductive liquid. Or they can be made of zigzagged conductors. For example, U.S. Pat. No. 8,469,741 describes examples of stretchable connectors.

Figure 9:
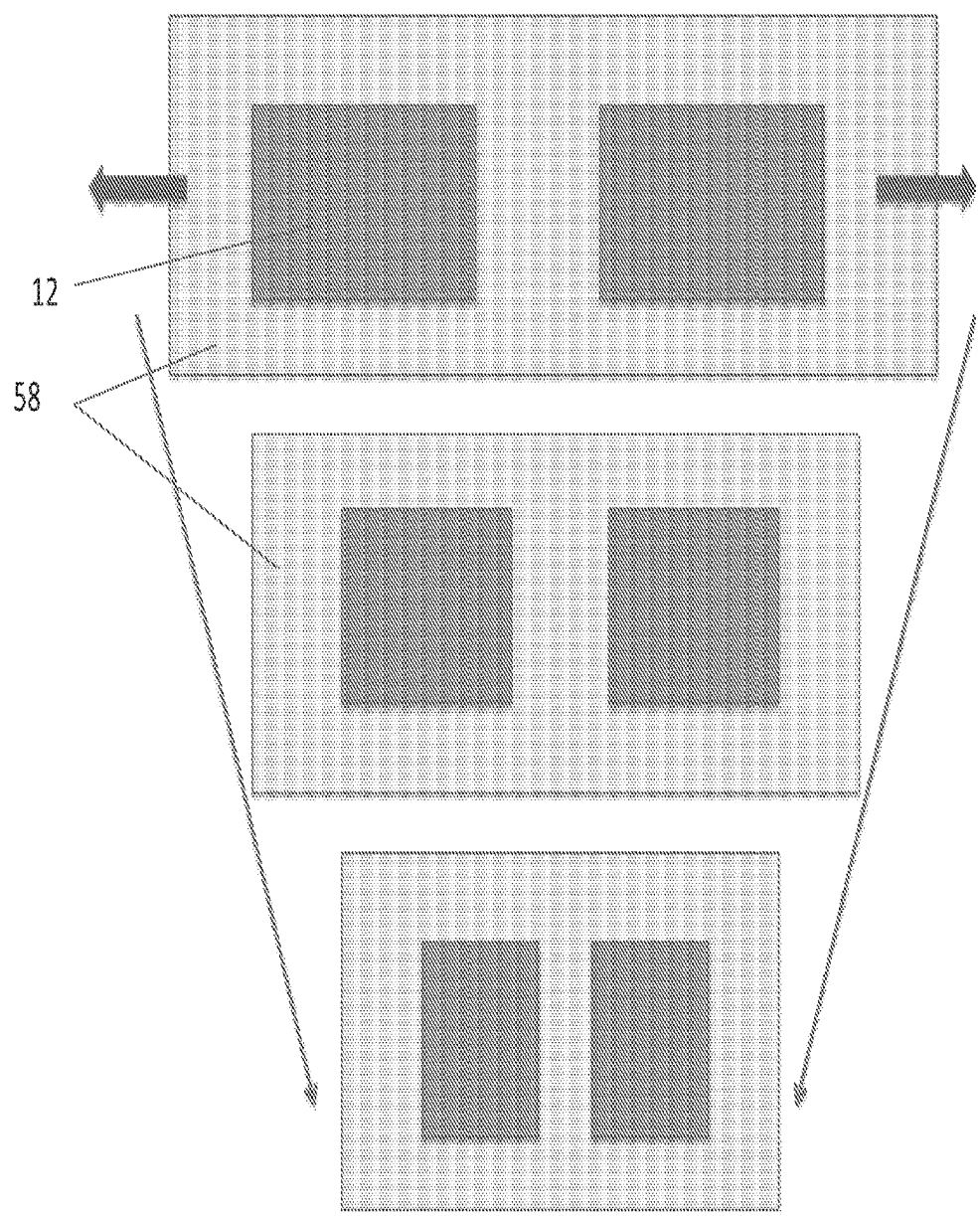
FIG. 9 illustrates on embodiment of a capacitive sensor of the present invention applied on a pre-stretched elastic substrate for forming a stretchable ECVT sensor.

FIG. 9 illustrates on embodiment of a capacitive sensor of the present invention applied on a pre-stretched elastic substrate 58 for forming a stretchable ECVT sensor. Conductive spray, liquid, or ink is applied to pre-stretched layer for forming conductive elements of integrative sensor layers. Elastic substrate can also be soaked in conductive liquid to form conductive parts of any layer in an integrative sensor. This concept can also be applied to the application of the signal traces.

Further details regarding the theory and application of ECVT, sensor design, image reconstruction, and deployment of an ECVT system are found in the U.S. Patent Application Publication US 2010/0097374 (application Ser. No. 11/909, 548), the relevant disclosures of which are included by reference thereto as if fully set forth herein.

As depicted in FIGS. 1A and 1B of the U.S. Patent Application Publication US 2010/0097374 referenced herein, an array of electrodes (e.g., capacitance plates) are arranged to form a capacitance sensor. In one application, this sensor may be placed around a pipe or vent to detect movement within the receptacle to provide imaging data. In a conventional ECVT system, the sensor is made up of capacitance plates where the capacitance is measure between a selected pair of plates. The principle of the basic measuring circuit involves connecting one plate (source electrode or sending electrode) of the sensor to a voltage (e.g., Vi) and another plate (detecting electrode or receiving electrode) to a capacitance measurement circuit.

In the preferred embodiment, the ECVT plates (i.e., electrodes) are comprised of an array of smaller capacitance segments that may be individually addressed. The shape of the capacitance segments can be made up various shapes where each plate can be activated with the same or different voltages, frequencies, or phase shifts. Segments of each electrode are preferably connected together in parallel, with voltage control applied independently to each segment. Segments of interest chosen to form sender or receiver plates can be activated by electronic switches that open or close to connect a particular segment in parallel with others chosen in same plate. For example, each segment may be activated with different amplitudes, phase shifts, or frequency to provide the desired sensitivity matrix distribution. In one embodiment, the array of selected capacitance segments can form many pairs of capacitance electrodes or plates without reducing overall plate size. The capacitance segments can also be joined in different configurations to provide different designs.

The sensor electronics of the present invention is designed to detect and measure the capacitance for the adaptive ECVT sensor of the present invention. For example, the difference in electrical energy stored in the adaptive ECVT sensor would be measured between an empty state and a state where an object is introduced into the imaging domain (e.g., between the electrodes). The change in overall energy of the system due to the introduction of a dielectric material in the imaging domain is used to calculate the change in capacitance related to the dielectric material. The change in capacitance can be calculated from the change in stored energy. Sensor electronics can also be designed by placing individual segment circuits in parallel yielding a summation of currents representing total capacitance between segments under interrogation. By individually addressing the capacitance segments of the electrodes of the present invention, electric field distribution inside the imaging domain can be controlled to provide the desired sensitivity matrix, focus the electric field, and increase overall resolution of reconstructed images.

Figure 10:
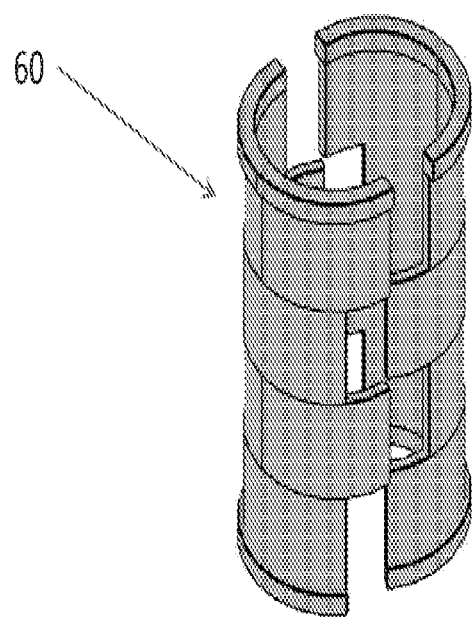
FIG. 10 illustrates one embodiment of a modular and removable section.

FIG. 10 illustrates one embodiment of a modular and removable section 60 through which the integrative flexible sensor of the present invention can be placed on the outside or on the inside. Removable sections are introduced as means of placing integrative sensors on fixed structures.

What is claimed is:

1. A flexible capacitance sensor for communicating signals to a data acquisition system for reconstructing an image of an area or object located in a subject being sensed, comprised of:
   a flexible layer of capacitance plates;
   a plurality of electrical lines for communicating signals from the capacitance plates to the data acquisition system;
   wherein the capacitance sensor is flexible and adapted to be wrapped around the subject being sensed;
   wherein the capacitance plates in the flexible layer of capacitance plates are individually addressable; and
   wherein the sensor is adapted to communicate signals to the data acquisition system for use in reconstructing an image of the area or object between the capacitance plates.

2. A flexible capacitance sensor according to claim 1, wherein the electrical lines are signal traces, wherein the sensor is further comprised of:
   a flexible shielding ground layer in between the layer of capacitance plates and the plurality of signal traces;
   a first flexible isolative layer between the flexible layer of capacitance plates and the flexible shielding ground layer;
   a second flexible isolative layer between the flexible shielding ground layer and the plurality of signal traces.

3. A flexible capacitance sensor according to claim 2, wherein the first and second flexible isolative layers are resistive for providing a path to discharge static charges from the flexible layer of capacitance plates to the flexible shielding ground layer.

4. A flexible capacitance sensor according to claim 1, further comprised of:
   a flexible insulation layer for separating the subject being sensed and the flexible layer of capacitance plates.

5. A flexible capacitance sensor according to claim 1, further comprised of:
   a flexible ground layer for forming an outside layer of the sensor for shielding the sensor from outside interference.

6. A flexible capacitance sensor according to claim 1, wherein the capacitance plates are comprised of conductive spray on a nonconductive layer.

7. A flexible capacitance sensor according to claim 1, wherein the electrical lines are trace lines, and wherein the sensor is further comprised of a plurality of ground lines placed between the trace lines.

8. A flexible capacitance sensor according to claim 1, wherein all the layers of the flexible capacitance sensor are connected by an adhesive material.

9. A flexible capacitance sensor according to claim 1, wherein the electrical lines are signal traces, and wherein the sensor is further comprised of a plurality of through holes for providing a path to the plurality of signal traces.

10. A flexible capacitance sensor according to claim 1, wherein the capacitance plates are connected using stretchable connectors.

11. A flexible capacitance sensor according to claim 1, wherein the capacitance plates are applied on an elastic substrate.

12. A flexible capacitance sensor according to claim 11, wherein the conductive spray or liquid is applied to the elastic substrate to form the capacitance plates.

13. A flexible capacitance sensor for communicating signals to a data acquisition system for reconstructing an image of an area or object located in a subject being sensed, comprised of:
    a flexible layer of capacitance plates;
    a plurality of electrical lines for communicating signals from the capacitance plates to the data acquisition system;
    a flexible ground layer for forming an outside layer of the sensor for shielding the sensor from outside interference;
    wherein the capacitance sensor is flexible and adapted to be wrapped around the subject being sensed;
    wherein the capacitance plates in the flexible layer of capacitance plates are individually addressable; and
    wherein the sensor is adapted to communicate signals to the data acquisition system for use in reconstructing an image of the area or object between the capacitance plates.

14. A flexible capacitance sensor for communicating signals to a data acquisition system for reconstructing an image of an area or object located in a subject being sensed, comprised of:
    a flexible layer of capacitance plates;
    a plurality of electrical lines for communicating signals from the capacitance plates to the data acquisition system;
    a flexible insulation layer for separating the subject being sensed and the flexible layer of capacitance plates;
    wherein the capacitance sensor is flexible and adapted to be wrapped around the subject being sensed;
    wherein the capacitance plates in the flexible layer of capacitance plates are individually addressable; and
    wherein the sensor is adapted to communicate signals to the data acquisition system for use in reconstructing an image of the area or object between the capacitance plates.

* * * * *